United States Patent [19]

Orth et al.

[11] Patent Number: 4,564,700

[45] Date of Patent: Jan. 14, 1986

[54] PROCESS FOR THE PREPARATION OF FLUORENE-9-CARBOXYLIC ACID

[75] Inventors: Winfried Orth, Hassloch; Emmerich Pastorek, Hemsbach; Werner Fickert, Mannheim, all of Fed. Rep. of Germany

[73] Assignee: Rutgerswerke Aktiengesellschaft, Fed. Rep. of Germany

[21] Appl. No.: 552,459

[22] Filed: Nov. 16, 1983

[30] Foreign Application Priority Data

Nov. 27, 1982 [DE] Fed. Rep. of Germany ....... 3243981

[51] Int. Cl.[4] ...................... C07C 51/09; C07C 51/15; C07C 69/753
[52] U.S. Cl. ........................................ 562/405; 560/8; 562/423
[58] Field of Search ...................... 560/8; 562/405, 423

[56] References Cited

U.S. PATENT DOCUMENTS

| | | | |
|---|---|---|---|
| 2,367,632 | 1/1945 | Wallingford et al. | 560/190 |
| 2,376,837 | 5/1945 | Wallingford et al. | 560/190 X |
| 3,264,308 | 8/1966 | van der Stelt | 560/8 X |
| 3,369,044 | 2/1968 | Leonard et al. | 560/8 X |
| 3,598,564 | 8/1971 | Jacobi et al. | 560/8 X |
| 3,636,080 | 1/1972 | Brossi et al. | 560/75 X |
| 3,692,826 | 9/1972 | Patmore et al. | 562/423 |
| 3,718,690 | 2/1973 | Bushick et al. | 562/423 X |

FOREIGN PATENT DOCUMENTS 0003663 1/1982 Japan .................................. 562/423

OTHER PUBLICATIONS

*The Chemistry of Carboxylic Acids and Esters,* 1969, pp. 165–170, 173, Interscience Publishers, New York, Patai, ed.

*Primary Examiner*—Natalie Trousof
*Assistant Examiner*—Patricia M. Scott
*Attorney, Agent, or Firm*—Bierman, Peroff & Muserlian

[57] ABSTRACT

An improved process for the preparation of fluorene-9-carboxylic acid comprising reacting fluorene and a dialkyl carbonate with alkyls of 1 to 5 carbon atoms in the presence of a member of the group consisting of alkali metal hydrides or potassium alcoholate of an aliphatic alcohol of 1 to 5 carbon atoms, neutralizing the mixture and saponifying the resulting fluorene-9-carboxylic acid ester to obtain fluorene-9-carboxylic acid in good yields.

6 Claims, No Drawings

PROCESS FOR THE PREPARATION OF FLUORENE-9-CARBOXYLIC ACID

STATE OF THE ART

Fluorene-9-carboxylic acid is an important intermediate for the preparation of antidiabetic and anti-arrhythmic pharmaceuticals and has been prepared by numerous methods starting from difficult to produce fluorene derivatives or from fluorene. Most of the processes beginning with fluorene as illustrated by U.S. Pat. No. 3,692,826 are reactions with carbon dioxide in the presence of a condensation agent such as sodium, lithium, butyllithium, lithium azide, potassium amide, potassium phenolate, α-phenyl-isopropyl potassium, barium phenolite or diphenylurea and potassium carbonate. The known processes are uneconomical due to low yields as well as low yields per volume. Chem. Ber., Vol. 44 (1911), p. 206 and J.Chem. Soc., 1949, p. 2623 describe the reaction of fluorene with ester of oxalic acid to produce fluorene-9-carboxylic acid in a series of complicated, multiple steps which are not commerically economical. The large number of synthesis attempts and exotic methods illustrate the need for a new approach to prepare fluorene-9-carboxylic acid.

OBJECTS OF THE INVENTION

It is an object of the invention to provide an economical process for the preparation of fluorene-9-carboxylic acid from readily available fluorene in a few, simple steps.

This and other objects and advantages of the invention will become obvious from the following detailed description.

THE INVENTION

The novel process of the invention for the preparation of fluorene-9-carboxylic acid comprises reacting fluorene and a dialkyl carbonate with alkyls of 1 to 5 carbon atoms in the presence of a member of the group consisting of alkali metal hydrides and potassium alcoholate of an aliphatic alcohol of 1 to 5 carbon atoms, neutralizing the mixture and saponifying the resulting fluorene-9-carboxylic acid ester to obtain fluorene-9-carboxylic acid.

The starting fluorene is contained in high temperature coal tars at an average concentration of about 2% and is obtained in large scale commerical operations by redistillation of coal tar washing oil or by direct recovery of a fluorene fraction during the primary coal tar distillation and subsequent recrystallization from naphtha solvent for example if necessary after removal of phenols and bases.

The said fluorene will undergo a coupling reaction with a dialkyl carbonate and alkali metal hydride or potassium alcoholate at moderate temperatures to form alkyl fluorene-9-carboxylate according to the following reaction scheme

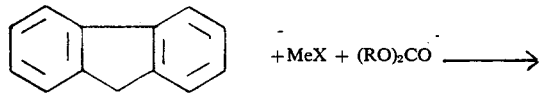

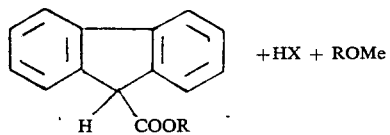

wherein Me is an alkali metal such as sodium or potassium, X is hydrogen or alcoholate and R is alkyl of 1 to 5 carbon atoms.

The reaction is unexpected since prior attempts to form esters using sodium amide normally used for couple reactions of this type have not been successful and the ester formation did not take place.

The fluorene used for this process can be a technical product with a purity of approx. 95%. The alkali metal hydride may also be potassium or sodium hydride e.g. using as sodium hydride an approx. 80% technical-grade product. The alkali metal hydride must be used in an amount corresponding at least to the stoichiometrically required quantity and the reaction proceeds with an especially good yield when the alkali hydride is added in a one-molar excess.

Potassium alcoholates suitable according to the invention are the potassium salts of all lower alkanols such as methanol, ethanol, propanol, isopropanol, butanol and its isomers as well as amyl alcohol and its isomers. It is important that the alcoholates do not contain any free alcohol and the potassium alcoholates are used in an amount at least equal to the required stoichiometric volume. The yields are improved if an excess is used in these cases.

A pure product may be used as dialkyl carbonate, e.g. dimethyl, diethyl, dipropyl or diisopropyl carbonate which produce the corresponding alkyl fluorene-9-carboxylates. Since these esters are subsequently saponified, mixtures of various dialkyl carbonates or mixed carbonates such as ethyl methyl carbonate or ethyl propyl carbonate may also be used. Ideally, the dialkyl carbonate used serves as a reactant as well as the solvent for the fluorene and this ensures that dialkyl carbonate is always present in an excess. When fluorene is dissolved in a different solvent such as benzene, toluene or xylene, the amount of dialkyl carbonate added must correspond to at least the stoichiometric amount. However, it was found that an economical yield was obtained best with dialkyl carbonate in an excess of more than four times the stoichiometric requirement and with a more than 15-fold stoichiometric excess, the reaction becomes uneconomical because of the large amount of solvent.

The process is preferably performed by suspending sodium hydride in an aromatic solvent and/or dialkyl carbonate and slowly adding a solution of fluorene in dialkyl carbonate. The conversion takes place with stirring at a temperature in the range from 40° to 80° C. over a period of 2-8 hours after which the reaction mixture is cooled and neutralized with cooling with an acid, preferably an aqueous solution of a strong inorganic acid. Then, possibly present contaminants are removed by filtration, the aqueous phase is separated and the organic solvent or solvent mixture is separated by distillation from the remaining organic phase and the 9-fluorene carboxylate remaining in the distillation residue is then saponified whereby fluorene-9-carboxylic acid precipitates in the form of light-beige crystals and is separated, washed and dried.

In the following examples there are described several preferred embodiments to illustrate the invention. However, it should be understood that the invention is not intended to be limited to the specific embodiments.

EXAMPLE 1

10% of a solution of 332 g (1.9 moles) of fluorene and 974 g (8.2 moles) of diethyl carbonate was added to a mixture of 974 g (8.2 moles) of diethyl carbonate and 120 g (4 moles) of sodium hydride in a reaction vessel and the mixture was heated at 65° C. with stirring. At the start of hydrogen evolution, nitrogen was introduced over the surface of the reaction mixture and the remaining 90% of the fluorene solution was added to the mixture at 65° C. over 90 minutes. The mixture was stirred at 60° C. for 4 hours and was cooled to 20° C. The reaction mixture was slowly poured into a mixture of 400 g (4 moles) of concentrated hydrochloric acid and 500 g of water cooled with water to prevent the temperature from rising above 40° C. The mixture was filtered and the filtrate was decanted. The organic phase was evaporated to dryness under reduced pressure and the distillate was 1700 ml of diethyl carbonate.

A mixture of the distillation residue, 1,049 g of acetic acid and 420 g of 10% hydrochloric acid was refluxed for 4 hours and after about 30 minutes, crystals of fluorene-9-carboxylic acid began to precipitate from the refluxing mixture. After the 4 hours, the mixture was cooled to 20° C. and was vacuum filtered. The recovered product was washed with 600 ml of toluene and then with 500 ml of water at which time the wash water was free of chloride ions. The 360 to 400 g of product was dried at 80° C. to obtain 322 g of fluorene-9-carboxylic acid in the form of light beige crystals melting at 226°–230° C. (80.7% yield based on fluorene).

EXAMPLE 2

The process of Example 1 was repeated using one liter of toluene in place of 974 g of diethyl carbonate to obtain 330 g of fluorene-9-carboxylic acid in the form of light beige crystals melting at 226°–230° C. (82.7% yield based on fluorene).

EXAMPLE 3

A solution of 332 g (1.9 moles) of fluorene and 974 g (8.2 moles) of diethyl carbonate was added with cooling to keep the temperature no higher than 40° C. to a mixture of 584 g (4.6 moles) of diethyl carbonate and 186 g (2.2 moles) of potassium ethylate in a reaction vessel and the mixture was stirred at 65°–70° C. for 5 hours and was cooled to 20° C. The mixture was slowly poured into a solution of 220 g (2.2 moles) of hydrochloric acid and 500 g of water with cooling to keep the temperature at a maximum of 40° C. The product was then treated as in Example 1 to obtain 280 g of fluorene-9-carboxylic acid in the form of light-beige crystals melting at 227°–229° C. (72.7% yield based on fluorene).

Various modifications of the process of the invention may be made without departing from the spirit or scope thereof and it is to be understood that the invention is intended to be limited only as defined in the appended claims.

What we claim is:

1. A process for the preparation of fluorene-9-carboxylic acid comprising reacting fluorene and at least a stoichiometric amount of a dialkyl carbonate with alkyls of 1 to 5 carbon atoms in the presence of an at least stoichiometric amount of a member of the group consisting of alkali metal hydrides or potassium alcoholate of an aliphatic alcohol of 1 to 5 carbon atoms, neutralizing the mixture and saponifying the resulting fluorene-9-carboxylic acid ester to obtain fluorene-9-carboxylic acid.

2. The process of claim 1 wherein the alkali metal hydride is sodium hydride.

3. The process of claim 2 wherein sodium hydride is present in a one molar excess.

4. The process of claim 1 wherein the reaction with fluorene is effected at 40° to 80° C.

5. The process of claim 1 wherein the dialkyl carbonate is used in a 4 to 15 molar excess.

6. The process of claim 3 wherein the dialkyl carbonate is used in a 4 to 15 molar excess.

* * * * *